(12) United States Patent
Melder et al.

(10) Patent No.: US 6,469,214 B2
(45) Date of Patent: Oct. 22, 2002

(54) PROCESS FOR THE PREPARATION OF ETHANOLAMINES

(75) Inventors: Johann-Peter Melder, Böhl-Iggelheim; Gerhard Schulz, Bad Dürkheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/995,751

(22) Filed: Nov. 29, 2001

(65) Prior Publication Data

US 2002/0115890 A1 Aug. 22, 2002

(30) Foreign Application Priority Data

Dec. 1, 2000 (DE) .......................... 100 59 629

(51) Int. Cl.[7] ..................... C07C 209/54; C07C 209/62; C07C 209/64; C07C 209/84
(52) U.S. Cl. .......... 564/478; 564/486; 564/499
(58) Field of Search ................ 564/478, 486, 564/499

(56) References Cited

U.S. PATENT DOCUMENTS

| 4,264,776 A | 4/1981 | Hershmann et al. ......... 564/384 |
| 4,328,370 A | 5/1982 | Fazo ........................... 564/486 |
| 5,545,757 A | 8/1996 | Hammer et al. ............. 564/475 |
| 5,693,866 A | 12/1997 | Roling et al. ............... 564/497 |

FOREIGN PATENT DOCUMENTS

| EP | 0 673 920 | 9/1995 |
| GB | 760215 | 10/1956 |

*Primary Examiner*—Brian J. Davis
(74) *Attorney, Agent, or Firm*—Keil & Weinkauf

(57) ABSTRACT

A process for the preparation of one or more ethanolamines (I), chosen from the group consisting of monoethanolamine, diethanolamine and triethanolamine, by conversion of one or more ethanolamines (II) different from the ethanolamine(s) (I), chosen from the group consisting of monoethanolamine, diethanolamine, triethanolamine. O,N,N-tris(2-hydroxyethyl) ethanol-N-(2-aminoethyl)-ethanolamine, N-(2-amine, hydroxy ethyl) piperazine, N-(2-hydroxyethyl)morpholine and N,N'-bis(2-hydroxyethyl) piperazine, where the ethanolamine(s) (II), optionally in the presence of ammonia, is/are treated with a strong base.

10 Claims, No Drawings

PROCESS FOR THE PREPARATION OF ETHANOLAMINES

The invention relates to a process for the preparation of ethanolamines (I) by conversion of ethanolamines (II) different from these.

Alkanolamines are basis products for a large number of industrial applications.

Ethanolamines, such as triethanolamine (TEA), or secondary products thereof are used, for example, in washing liquids for gas washes, in crop protection compositions, soaps, laundry detergents and shampoos, and as dispersants and emulsifiers.

Ethanolamines can be prepared by hydroxyethylation of amines by reaction of the amines with ethylene oxide, see Ullmann's Encyclopedia of Industrial Chemistry, chapter on ethanolamines and propanolamines-N-alkylated ethanolamines.

Monoethanolamine (MEA), diethanolamine (DEA) and triethanolamine (TEA) are prepared by reacting ammonia with ethylene oxide in the liquid phase under pressure and at elevated temperature, as described in GB-A-760 215 or EP-A-673 920.

In this process, an ethanolamine mixture is formed which comprises, as main components, MEA, DEA and TEA, which is then worked up by distillation in a plurality of stages. The composition of the resulting ethanolamine mixture can only be varied within narrow limits as a consequence of the process. In the preparation of an ethanolamine, for example of DEA, the other ethanolamines (MEA, TEA) thus automatically form as coupling products. If, for example, there is a high requirement for DEA, then this can only be satisfied under some circumstances by an overproduction of the coupling products MEA and TEA being accepted.

There has therefore been no lack of attempts to produce a particular ethanolamine by conversion of other ethanolamines.

U.S. Pat. No. 4,264,776 describes the catalytic oxidation of tertiary amines with oxygen to secondary amines in the presence of an active carbon catalyst. According to Example 2 of this patent specification, TEA is reacted over active carbon at 115° C. with 60% conversion to DEA with undefined selectivity. A $C_2$ radical of the TEA is degraded oxidatively in the process, e.g. to formic acid.

U.S. Pat. No. 4,328,370 describes the conversion of lower trialkanolarnines to mono and dialkanolamines by reaction with ammonia at elevated temperature in the presence of a hydrogenation catalyst. According to the examples of this patent specification, TEA can be reacted with ammonia in the presence of Pd/C or $Pd/Al_2O_3$ and optionally $H_2$ at 200 to 300° C. to give DEA and MEA. The selectivity of the formation of DEA and MEA decreases with increasing conversion. The total yield of MEA and DEA (sum) is up to 50% at a conversion of 66% and a selectivity of 79.7%.

U.S. Pat No. 5,693,866 describes the treatment of alkanolamines with alkali metal hydroxides for the purpose of improving the color quality of the alkanolamines, the alkanolamines being chemically unchanged. In the examples, TEA is treated with NaOH at temperatures of from 165 to 176° C. over a period of from 3 to 65 h.

It is an object of the present invention to provide an economic and efficient process for the preparation of one or more ethanolamines (I) from one or more ethanolamines (II) different from the ethanolamines (I) in order to utilize ethanolamines (II) produced in excess in an economically sensible manner.

We have found that this object is achieved by a process for the preparation of one or more ethanolamines (I), chosen from the group consisting of monoethanolamine, diethanolamine and triethanolamine, by conversion of one or more ethanolamines (II) different from the ethanolamine(s) (I), chosen from the group consisting of monoethanolamine, diethanolamine, triethanolamine, O,N,N-tris (2-hydroxyethyl)ethanolamine, N-(2-amino ethyl) ethanolamine, N-(2-hydroxyethyl)piperazine, N-(2-hydro-xyethyl) morpholine and N,N'-bis(2-hydroxyethyl) piperazine, where the ethanolami ammonia, is/are treated with a strong base.

The ethanolamine(s) (I) can be prepared from a single ethanolamine (II) or a mixture of two or more ethanolamines (II).

For example, diethanolamine can be obtained by treatment of pure monoethanolamine or of pure triethanolamine with a strong base. Monoethanolamine can be obtained by treatment of pure diethanolamine. In addition, triethanolamine is generally obtained.

Diethamolamine is preferably prepared by treatment of a mixture comprising monoethanolamine and triethanolamine with a strong base. Preferred mixtures comprise TEA and MEA in the molar ratio from 10:1 to 1:10.

The treatment of the ethanolamine(s) (I) can be carried out in the presence of ammonia. For example, diethanolamine can be prepared by treatment of a mixture comprising triethanolamine and ammonia.

In addition, monoethanolamine is generally obtained. Preferred mixtures comprise TEA and ammonia in the molar ratio of from 10:1 to 1:20.

Monoethanolamine can also be obtained by treatment of a mixture comprising diethanolamine and ammonia.

Said ethanolamine mixtures used in the conversion can comprise further ethanolamines. It is also possible to use complex ethanolamine mixtures which comprise two or more or all of the ethanolamines (II) listed above. The starting ethanolamine mixture can in part already comprise the ethanolamine(s) (I) to be prepared. Examples are technical grade ethanolamine mixtures as can be obtained by the following processes:

by reaction of ammonia or of a primary or secondary amine with ethylene oxide. e.g. in accordance with EP-A-673 920:

by 1,4-addition of ammonia or of a primary or secondary amine to an α,β-unsaturated aldehyde, such as acrolein, and subsequent hydrogenation;

by 1,4-addition of ammonia or of a primary or secondary amine to an α,β-unsaturated acid.such as acrylic acid, or to an α,β-unsaturated ester, such as acrylic ester. and subsequent reduction., e.g. by hydrogenation:

by 1,4-addition of water to an α,β-unsaturated nitrile, such as acrylonitrile, and subsequent reduction, e.g. by hydrogenation;

by amination of primary or secondary alcohols or reductive amination of hydroxyaldehydes or hydroxyketones. N-(2-Aminoethyl)ethanolamine (AEEA) can be obtained by reaction of monoethanolamine or ammonia with ethylene oxide in the presence of hydrogen and a hydrogenation, dehydrogenation or amination catalyst.

Preference is given to starting from ethanolamine mixtures which do not comprise the product of value (the ethanolamine (I) to be prepared) since the product of value can also gradually be degraded under the reaction conditions.

It is assumed that, under the action of strong bases, there is a cleavage of ethanolamines with n 2-hydroxy-ethyl groups into the next lower ethanolamine with n−1 2-hydroxyethyl groups and ethylene oxide. The ethylene oxide which is formed as an intermediate is scavenged by an acceptor, preferably ammonia or monoethanolamine, to form the corresponding next higher ethanolamine. It is therefore preferred according to the invention to prepare an ethanolamine with n 2-hydroxyethyl groups from a mixture of an ethanolamine with n+1 2-hydroxyethyl groups and an ethanolamine with n−1 2-hydroxyethyl groups or ammonia. Ethylene oxide is also released from the other ethanolamines specified (O,N,N-tris (2-hydroxyethyl)ethanolamine, N-(2-amino ethyl) ethanolamine, N-(2-hydroxyethyl)piperazine, N-(2-hydroxyethyl)morpholine and N,N'-bis(2-hydroxy ethyl) piperazine), which generally do not represent a product of value. These may therefore be likewise advantageously present in the starting mixture. The 2-hydroxyethylamino units (HO-CH$_2$-CH$_2$-N) present in the starting material mixture are largely retained overall.

The process according to the invention makes it possible, in particular, to convert economically significant ethanolamines, such as MEA, DEA and TEA, into one another, in particular to prepare DEA from MEA and/or TEA. By-products produced in this reaction are coupling products, such as N,N'-bis (2-hydroxyethyl)piperazine. O-ethoxylated products, such as O-(2-hydroxyethyl)triethanolamine, and products with higher degrees of ethoxylation. In contrast to the prior art, however, these products are not discarded, but can be used, for example, as cement auxiliaries.

The ethanolamine(s) (II) is/are treated with a strong base. Suitable bases are all strong bases which are able to deprotonate ethanolamines to a noteworthy degree. Preferred strong bases are basic alkali metal and alkaline earth metal hydroxides, alkali metal alkoxides, and basic metal oxides, such as oxides of the rare earth metals, for example LiOH, NaOH, KOH, CsOH, Ba(OH)$_2$, Ca(OH)$_2$, sodium methoxide, sodium ethoxide, potassium t-butoxide and lanthanum oxide. The bases can be used as solid or as aqueous or alcoholic solution. Particularly preferred strong bases are NaOH and KOH.

The ethanolamine(s) (II) can be present dissolved or dispersed in an inert solvent. Suitable solvents are alcohols, such as methanol, ethanol, isopropanol, n-butanol, 2-ethylhexanol, ethers, such as tetrahydrofuran and 1,4-dioxane, aliphatic and aromatic hydrocarbons or mixtures thereof, such as pentane, hexane, heptane, petroleum ether, benzene, toluene, xylene, Mihagol and water.

The process according to the invention is generally carried out at temperatures above 180° C., preferably at 180 to 270° C., particularly preferably at 190 to 260° C., and in particular at 200 to 250° C. in customary reaction apparatuses, such as autoclaves, tubular reactors or stirred-tank reactors. The reaction time is preferably between 0.5 and 20 h and is governed by the composition of the starting mixture, the desired product of value, the strong base used and the reaction temperature. The choice of these parameters can be optimized directly by the person skilled in the art by a few exploratory experiments. Reaction times which are too long may reduce the yield of the product of value since the product of value may also be subjected to cleavage under the reaction conditions. It is particularly preferable to continuously remove the product of value formed, for example by distillation, from the reaction mixture and thus to protect it against degradation.

The invention is described in more detail by the examples below.

EXAMPLES

Reaction of TEA in the presence of ammonia

Comparative Example C1

60 g of TEA and 30 g of ammonia are stirred at 250° C. for 3 h in a stirred autoclave without the addition of a basic compound.

Example 1

60 g of TEA, 27 g of ammonia and 6 g of KOH are stirred at 250° C. for 3 h in a stirred autoclave.

Example 2

60 g of TEA, 32 g of ammonia and 6 g of NaOH are stirred at 250° C. for 3 h in a stirred autoclave.

A sample is then removed from the reactor space, cooled, derivatized with trifluoroacetic anhydride and quantitatively analyzed using gas chromatography against diethylene glycol dimethyl ether as internal standard.

The results of the experiments are given in Table 1.

TABLE 1

| Example | MEA [% by wt.] | DEA [% by wt.] | DIHEP* [% by wt.] | TEA ether** [% by wt.] | TEA conversion [%] | MEA selectivity [mol %] | DEA selectivity [mol %] |
|---|---|---|---|---|---|---|---|
| C1 | 0.54 | 1.69 | 0.00 | 0.74 | 10.3 | 12.6 | 23.2 |
| 1 | 6.08 | 20.86 | 0.87 | 1.21 | 84.7 | 17.5 | 35.0 |
| 2 | 12.56 | 10.69 | 3.67 | 0.67 | 95.7 | 21.1 | 19.7 |

*N,N'-bis(2-hydroxyethyl)piperazine
**O-(2-hydroxyethyl)triethanolamine

Compared with the comparative example, it is clear that in the presence of NaOH or KOH the lower ethanolamines MEA and DEA are obtained with considerably increased conversions and with at least comparable selectivity.

Reaction of TEA and MEA

General procedure

Unless stated otherwise, 20 g of TEA (0.13 mol) and 10 g of MEA (0.16 mol) are premixed with 2 g of the given strongly basic compound in a 50 ml stirred autoclave and stirred at the given temperature for the given time. A sample is then taken from the reactor space, cooled, derivatized with trifluoroacetic anhydride and quantitatively analyzed by gas chromatography against diethylene glycol dimethyl ether as internal standard.

In the examples below, deviations from the general procedure were made.

Comparative Example C2

The MEA/TEA mixture is heated without the addition of a basic compound.

Example 3

30 g of TEA are heated with 2 g of KOH.

Example 4

30 g of MEA are heated with 2 g of KOH.

Example 13

24 g of TEA and 6 g of MEA are heated with 2.4 g of KOH.

Example 19

The MEA/TEA mixture is heated with 2 g of NaOH dissolved in 2 g of water.

Example 20

The MEA/TEA mixture is heated with 2 g of NAOH dissolved in 5 g of ethanol.

The results of the experiments are given in Table 2.

the conversion proceeds not only from higher ethanolamines to lower ethanolamines, but also vice versa (Examples 3 and 4).

We claim:

1. A process for the preparation of one or more ethanolamines (I), chosen from the group consisting of monoethanolamine, diethanolamine and triethanolamine, by conversion of one or more ethanolamines (II) different from the ethanolamine(s) (I), chosen from the group consisting of monoethanolamine, diethanolamine, triethanolamine, O,N,N-tris (2-hydroxyethyl) ethanolamine, N-(2-aminoethyl) ethanolamine, N-(2-hydroxvethyl)piperazine N-(2-hydroxyethyl) morpholine and N,N'-bis(2-hydroxyethyl) piperazine, where the ethanolamine(s) (II), optionally in the presence of ammonia, is/are treated with a strong base.

2. A process as claimed in claim 1 for the preparation of diethanolamine, where monoethanolamine is treated.

3. A process as claimed in claim 1 for the preparation of diethanolamine, where triethanolamine is treated.

4. A process as claimed in claim 1 for the preparation of diethanolamine, where a mixture comprising monoethanolamine and triethanolamine is treated.

5. A process as claimed in claim 1 for the preparation of diethanolamine and optionally monoethanolamine, where a mixture comprising triethanolamine and ammonia is treated.

TABLE 2

| Example | Basic catalyst | Time [h] | Temp. [° C.] | MEA [% by wt.] | DEA [% by wt.] | TEA [% by wt.] | AEEA*** [% by wt.] | DIHEP* [% by wt.] | TEA ether** [% by wt.] | TEA conversion [%] | MEA conversion [%] |
|---|---|---|---|---|---|---|---|---|---|---|---|
| C2 | — | 24 | 200 | 26.9 | 0.6 | 65.9 | 0.7 | 0.0 | 0.3 | 1.2 | 19.2 |
| 3 | KOH | 2 | 250 | 0.1 | 4.5 | 65.5 | 0.0 | 0.5 | 1.5 | 34.5 | — |
| 4 | KOH | 1.8 | 250 | 29.4 | 7.2 | 0.2 | 5.8 | 0.0 | 0.9 | — | 60.6 |
| 5 | KOH | 20 | 200 | 19.4 | 7.7 | 51.1 | 2.1 | 0.4 | 0.3 | 23.4 | 41.7 |
| 6 | NaOMe | 20 | 200 | 20.1 | 2.4 | 48.7 | 2.1 | 0.2 | 0.3 | 27.0 | 39.6 |
| 7 | KOH | 20 | 250 | 0.4 | 1.9 | 6.4 | 1.2 | 6.2 | 0.2 | 90.4 | 98.8 |
| 8 | KOH | 6 | 250 | 3.1 | 17.1 | 15.4 | 2.8 | 4.3 | 0.8 | 76.9 | 90.7 |
| 9 | KOH | 2 | 250 | 6.5 | 20.2 | 31.3 | 2.4 | 2.4 | 1.3 | 53.1 | 80.5 |
| 10 | KOH | 22.5 | 220 | 6.8 | 15.8 | 33.9 | 3.8 | 3.8 | 1.0 | 49.2 | 79.6 |
| 11 | NaOH | 1.3 | 250 | 9.6 | 22.7 | 32.2 | 2.2 | 2.0 | 1.8 | 51.7 | 71.2 |
| 12 | LiOH | 7 | 250 | 7.6 | 19.9 | 28.7 | 5.2 | 6.9 | 1.5 | 57.0 | 77.2 |
| 13 | KOH | 3 | 250 | 3.3 | 21.9 | 32.4 | 1.5 | 3.2 | 1.0 | 83.5 | 59.5 |
| 14 | Ca(OH)$_2$ | 24 | 250 | 9.8 | 8.3 | 37.4 | 4.3 | 2.9 | 0.5 | 43.9 | 70.6 |
| 15 | CsOH | 5 | 250 | 8.6 | 13.4 | 38.1 | 4.0 | 2.7 | 1.0 | 42.9 | 74.2 |
| 16 | KOtBu | 6.3 | 250 | 7.9 | 13.9 | 29.9 | 4.2 | 2.8 | 1.1 | 55.2 | 76.3 |
| 17 | Ba(OH)$_2$ | 22 | 250 | 13.3 | 8.6 | 40.8 | 4.9 | 2.6 | 0.7 | 38.8 | 60.1 |
| 18 | La$_2$O$_3$ | 22 | 250 | 16.3 | 6.9 | 41.2 | 3.6 | 1.9 | 0.7 | 38.2 | 51.1 |
| 19 | NaOMe | 6.5 | 250 | 11.6 | 10.9 | 36.7 | 3.8 | 2.8 | 0.8 | 45.0 | 65.2 |
| 20 | NaOEt | 6.4 | 250 | 18.4 | 4.1 | 47.9 | 2.9 | 1.3 | 0.6 | 28.2 | 44.7 |
| 21 | NaOH + H$_2$O | 1.5 | 250 | 12.5 | 20.9 | 26.6 | 2.1 | 1.9 | 1.5 | 60.1 | 62.5 |
| 22 | NaOH + EtOH | 1.4 | 250 | 7.4 | 22.5 | 25.0 | 1.7 | 2.2 | 1.6 | 62.5 | 77.8 |

*N,N'-bis(2-hydroxyethyl)piperazine
**O-(2-hydroxyethyl)triethanolamine
***N-(2-aminoethyl)ethanolamine From the examples it is clear that the addition of an acceptor, such as ammonia or MEA, increases the yield of ethanolamine (1) (Examples 3, 4 and 9);

reaction time and temperature are to be matched to the basic compound (Examples 5 to 22);

the reaction is preferably terminated at a partial conversion of the starting ethanolamines (MEA and TEA) since the product of value formed (DEA) is degraded (Examples 7 to 9);

the basic compound can also be added as solution (Examples 21 and 22);

6. A process as claimed in claim 1, where the strong base used is an alkali metal base. an alkaline earth metal base or an alkali metal alkoxide.

7. A process as claimed in claim 6, where the strong base used is sodium hydroxide or potassium hydroxide.

8. A process as claimed in claim 6, where the strong base is used as aqueous or alcoholic solution.

9. A process as claimed in claim 1, where the ethanolamine(s) is/are present dissolved in an inert solvent.

10. A process as claimed in claim 1, where the treatment is carried out at 180° C. to 270° C. over a period of 0.5 h to 20 h.

* * * * *

UNITED STATES PATENT AND TRADEMARK OFFICE
CERTIFICATE OF CORRECTION

PATENT NO.    : 6,469,214 B2
DATED         : October 22, 2002
INVENTOR(S)   : Melder et al.

It is certified that error appears in the above-identified patent and that said Letters Patent is hereby corrected as shown below:

<u>Title page,</u>
Item [57], ABSTRACT,
Line 4, "from the ethanolamine" should be -- from the ethanolamine(s) --;
Line 5, delete "(s)";
Line 8, "hydroxy ethyl" should be -- hydroxyethyl --.

<u>Column 6,</u>
Line 12, "hydroxvethyl" should be -- hydroxyethyl --.
Line 55, "base. an" should be -- base, an --.

Signed and Sealed this

Eighteenth Day of February, 2003

JAMES E. ROGAN
*Director of the United States Patent and Trademark Office*